United States Patent [19]
Harpstead et al.

[11] Patent Number: 5,697,951
[45] Date of Patent: Dec. 16, 1997

[54] IMPLANTABLE STIMULATION AND DRUG INFUSION TECHNIQUES

[75] Inventors: Stanley D. Harpstead, Manchester, Mass.; Lynn M. Otten, Blaine; Thomas R. Prentice, Lake Elmo, both of Minn.

[73] Assignee: Medtronic, Inc., Minneapolis, Minn.

[21] Appl. No.: 637,362

[22] Filed: Apr. 25, 1996

[51] Int. Cl.⁶ .................................................. A61N 1/02
[52] U.S. Cl. .................................. 607/3; 604/891.1
[58] Field of Search ................... 607/3, 4, 33, 120; 604/890.1, 891.1, 20, 21, 51, 93, 114

[56] References Cited

U.S. PATENT DOCUMENTS

| | | | |
|---|---|---|---|
| 4,146,029 | 3/1979 | Ellinwood, Jr. | 607/9 |
| 4,166,470 | 9/1979 | Neumann | 607/33 |
| 4,639,244 | 1/1987 | Rizk et al. | 604/19 |
| 5,087,243 | 2/1992 | Avitall | 607/120 |
| 5,314,458 | 5/1994 | Najafi et al. | 128/903 |
| 5,330,505 | 7/1994 | Cohen | 607/3 |
| 5,370,672 | 12/1994 | Fowler et al. | |
| 5,423,877 | 6/1995 | Mackey | |

FOREIGN PATENT DOCUMENTS 07605  5/1992  WIPO .................. 607/120

*Primary Examiner*—William L. Kamm
*Assistant Examiner*—George R. Evanisko
*Attorney, Agent, or Firm*—Banner & Witcoff, Ltd.

[57] ABSTRACT

An implantable system for infusing a fluid agent and providing electrical stimulation without requiring an implanted pump or implanted source of electrical energy. An implantable housing is fitted with a percutaneous fill port that communicates with a reservoir to hold a fluid agent, such as a drug. An antenna located inside the housing receives radio frequency power signals from an outside antenna. A pulse generator outside the housing receives power and information from the radio frequency signals to produce stimulation pulses. The pulses and the fluid agent are both transported by a catheter to a site of application in the body. A connector allows the stimulation pulses and fluid agent to be transported from the housing to the catheter while maintaining electrical isolation between the stimulating pulses and the fluid agent.

17 Claims, 4 Drawing Sheets

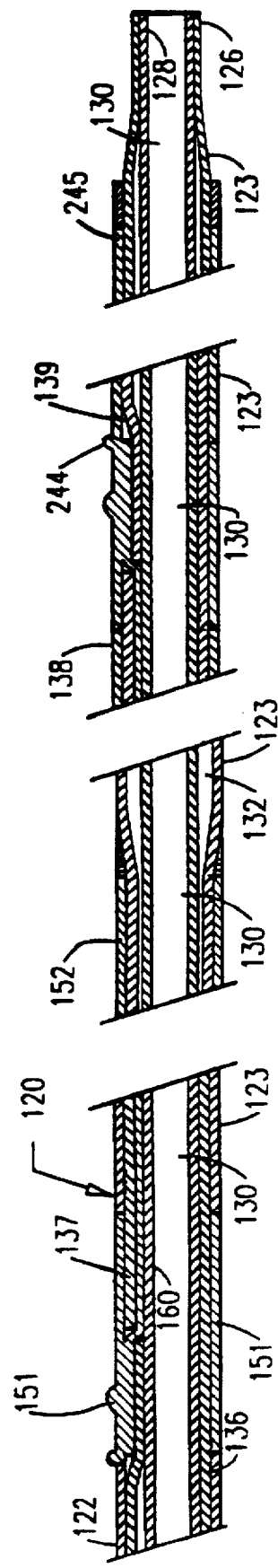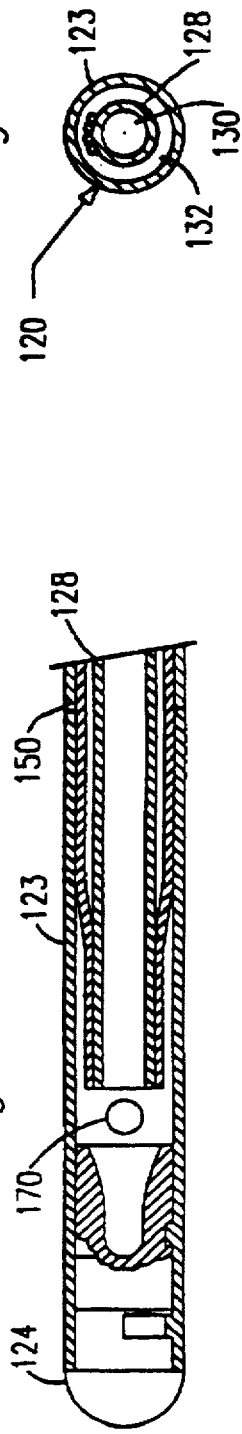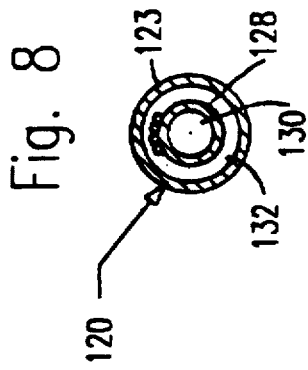

IMPLANTABLE STIMULATION AND DRUG INFUSION TECHNIQUES

BACKGROUND OF THE INVENTION

1. Field of the Invention

This invention relates to implantable electrical stimulation and drug infusion techniques, and more particularly relates to such techniques in which fluid pressure and electrical power are received from outside the implanted system.

2. Description of the Related Art

Catheters for simultaneously providing electrical stimulation and drug infusion have been devised in the past. One example is shown in U.S. Pat. No. 5,423,877 (Mackey, issued Jun. 13, 1995). Electrical stimulators also have been devised in which power and data are received by an implanted circuit via an antenna from an external power source and radio frequency generator. One example of such a stimulation system is shown in U.S. Pat. No. 5,314,458 (Najafi et al., issued May 24, 1994). Another neurological stimulation system utilizing a computer and transmitter located outside a body being stimulated is shown in U.S. Pat. No. 5,370,7672 (Fowler et al., issued Dec. 6, 1994).

The foregoing devices fail to provide a dual therapy of drug infusion and electrical stimulation, and are expensive and difficult to manufacture. As a result, they are unable to meet the need for a relatively short-term, low-cost combination of drug infusion and electrical stimulation therapy. Such short-term therapy is important for cancer pain management, when life expectancy does not warrant the high cost of a long-term implantable drug infusion pump and another implantable stimulation device, or when direct site delivery of drugs or radio isotopes is desired.

Enhancement of drug transport and affectivity electrical stimulation and/or electrical current can result in a reduction in the amount of a drug required for therapy, or may synergistically treat different symptoms, such as nociceptive and neuropathic pains. As a result, it is frequently advantageous to provide a system capable of administering both drugs and electrical stimulation. The present invention solves the need for such short-term therapy and overcomes the cost disadvantages of independently employing the prior known techniques.

SUMMARY OF THE INVENTION

A preferred form of the invention can be used for infusing a fluid agent, such as a drug, and for providing electrical stimulation to a body. The invention can be advantageously used in connection with a neurostimulator module coupled to an antenna and located outside the body, in combination with a conventional hypodermic needle that is coupled to a pump for providing the fluid agent under pressure to the needle.

In such an environment, the invention preferably takes the form of an implantable housing defining a first surface on a second surface. A percutaneous fill port is located adjacent the first surface. A reservoir is located inside the housing for holding the fluid agent at pressure maintained by the supply of the fluid agent admitted through the fill port, preferably by the hypodermic needle. An antenna is located inside the housing for receiving radio frequency power signals. Means also are located inside the housing and are coupled to the antenna for generating stimulation pulses from the radio frequency power signals received by the antenna. A catheter defines a fluid lumen for transporting the fluid agent through the catheter. The catheter includes one or more electrodes for administering electrical stimulation to a predetermined portion of the body, as well as one or more catheter conductors for transmitting the stimulation pulses to the one or more electrodes. Means are also provided for transporting the fluid agent from the fluid lumen to a predetermined portion of a body. Connector means enable the transmission of the stimulation pulses from the means for generating to the one or more catheter conductors. The connection means also enable transport of a fluid agent from the reservoir to the fluid lumen.

By using the foregoing techniques, a fluid agent and electrical stimulation can be administered and regulated to the body with a degree of cost effectiveness and efficiency unattainable by the use of prior art techniques. In particular, the administration can be accomplished without providing any source of fluid pressure inside the housing or any source of electrical power inside the housing. The resulting low cost of the system enables electrical stimulation and drug infusion to be used in cases for which much more expensive therapy is not warranted.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 3 is a cross-sectional view taken through the middle of fragment F3 of the catheter shown in FIG. 1;

FIG. 4 is a cross-sectional view taken through fragment F4 of the catheter shown in FIG. 1;

FIG. 5 is a cross-sectional view taken through the middle of fragment F5 of the catheter shown in FIG. 10;

FIG. 6 is a cross-sectional view taken through the middle of fragment F6 of the catheter shown in FIG. 10;

FIG. 7 is a cross-sectional view taken through the middle of fragment F7 of the catheter shown in FIG. 1;

FIG. 8 is a cross-sectional view of the catheter shown in FIG. 1 taken along line 8—8 of FIG. 1;

DESCRIPTION OF THE PREFERRED EMBODIMENTS

Figure 1:
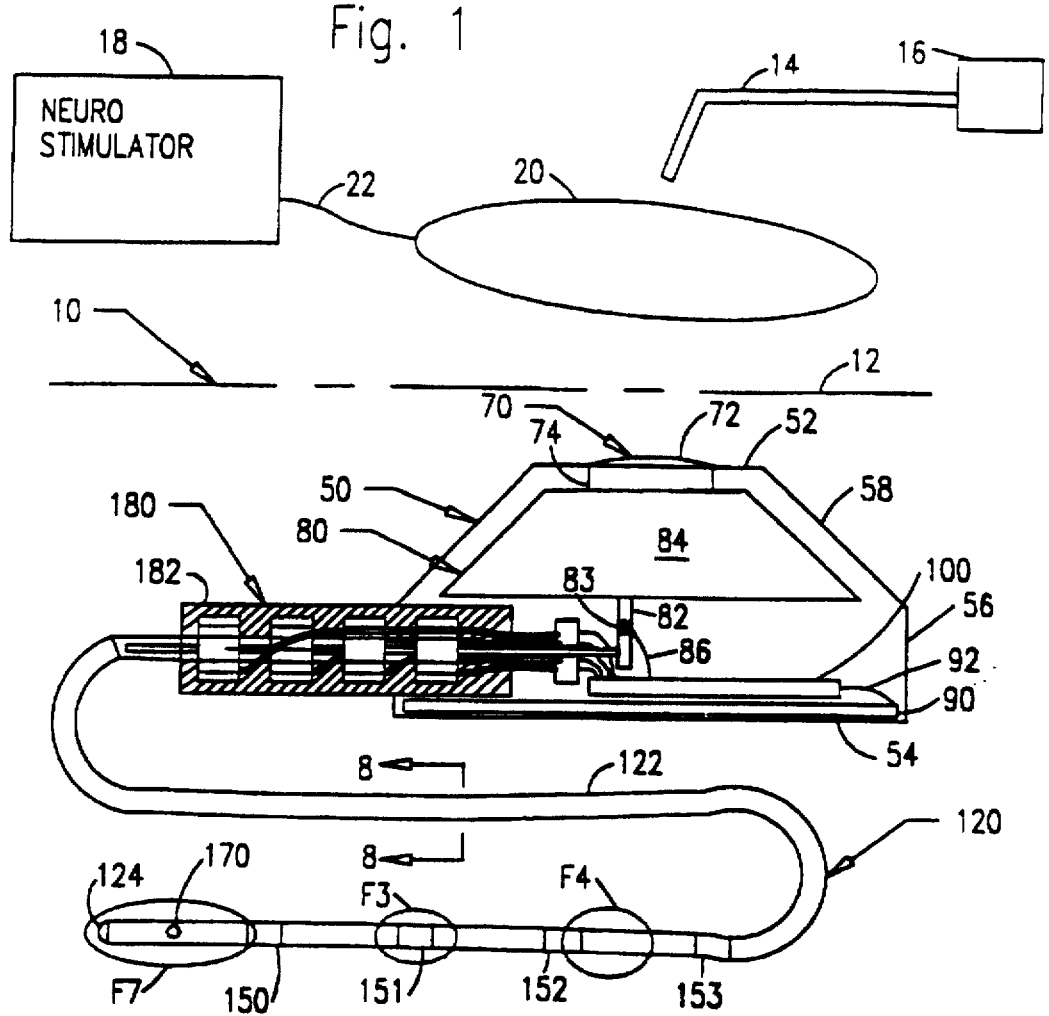
FIG. 1 is a fragmentary, partially diagrammatic, side elevational view of a preferred form of the invention in which a preferred form of connector assembly is shown in cross-section attached to a catheter.

Referring to FIG. 1, a preferred form of the invention is useful for providing drug infusion and electrical stimulation therapy to a body 10 of a living organism having a skin 12. A fluid agent, such as a drug, may be administered through a hypodermic needle 14 that is connected to a fluid coupling 16 of a conventional pump useful for infusing drugs (not shown). A conventional neurostimulator 18 is used to generate data and an electrical power signal suitable for producing stimulation pulses by transmitting radio frequency electrical energy from an antenna 20. The radio frequency power signal is transmitted to antenna 20 through an antenna lead 22. Neurostimulators are known in the art and are described in detail in U.S. Pat. Nos. 5,370,672 and 5,314,458.

Figure 2:
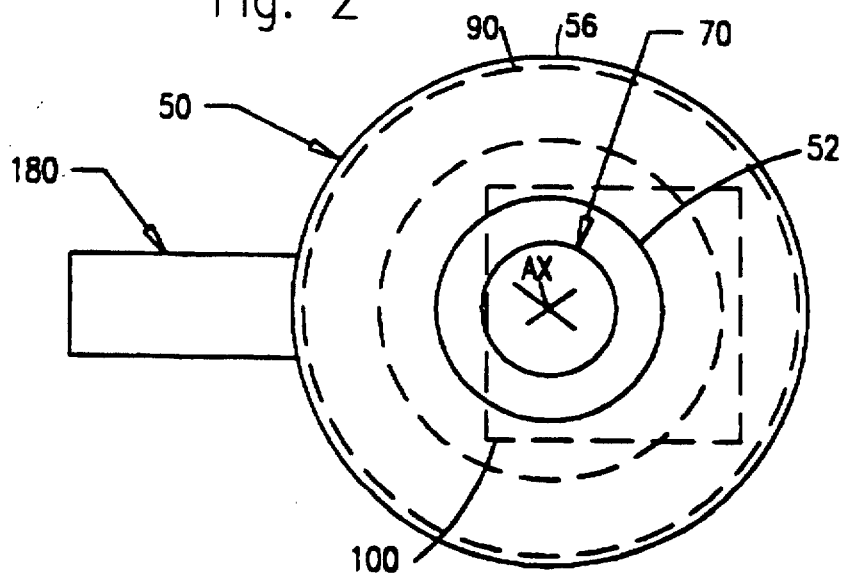
FIG. 2 is a top plan view of the implanted portion of the apparatus shown in FIG. 1 with the catheter removed.

Referring to FIGS. 1 and 2, a preferred form of implantable system made in accordance with the present invention comprises a housing 50 having a top surface 52, a bottom surface 54, a cylindrical side wall 56 and a conical wall 58.

Surface 52 is fitted with a conventional percutaneous fill port 70 comprising a conventional membrane 72 that can be penetrated by hypodermic needle 14 and is self-sealing after the needle is removed. Fluid agent received from needle 14 is conducted through a conventional funnel 74 to a fluid agent reservoir 80 having an outlet tube 82 that is fitted with a conventional valve 83. The rate of flow of fluid agent 84 from reservoir 80 to catheter 120 is controlled by valve 83 based on control signals transmitted over a conductor 86. The reservoir holds fluid agent 84 received under pressure from needle 14 and preserves the pressure provided through needle 14 so that the fluid agent, such as drugs, may be infused into body 10.

Figure 10:
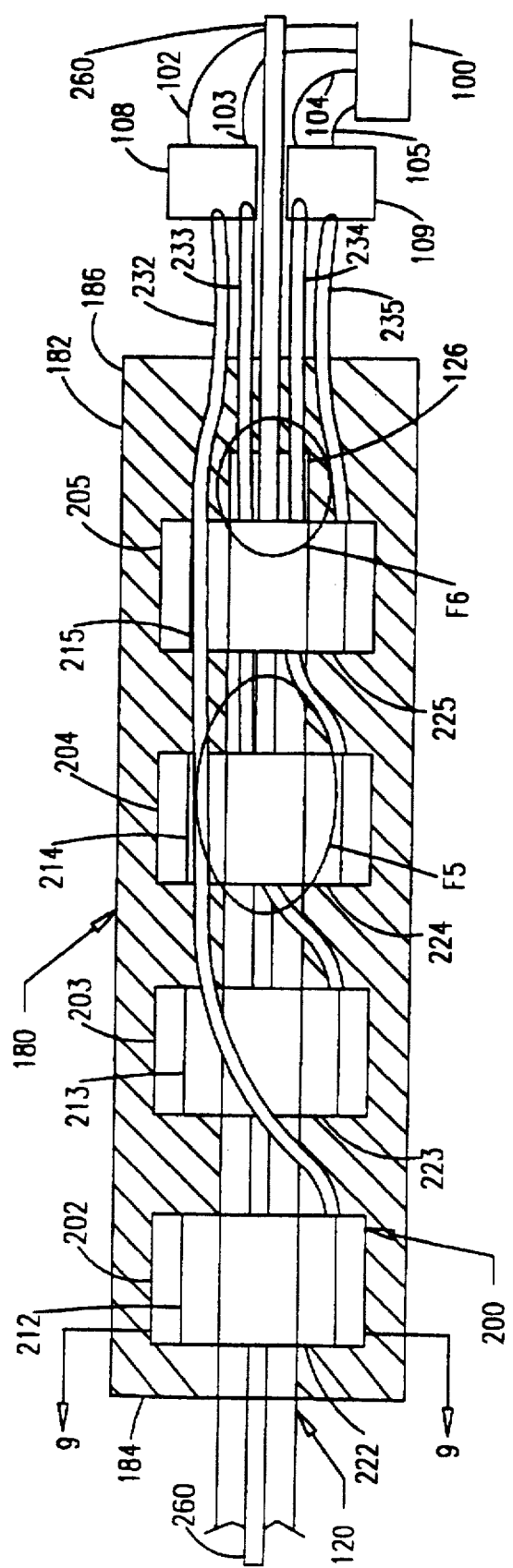
FIG. 10 is an enlarged view of the connector assembly shown in FIG. 1.

A conventional implantable antenna 90 is located adjacent surface 54 as shown. The antenna is coupled by a conductor 92 to a conventional implantable pulse generator 100. The pulse generator is powered by the electrical power signal received by antenna 90 from antenna 20. Antenna 90 also receives data from antenna 20 in a well-known manner by modulating the radio frequency signals transmitted by antenna 20. By well-known techniques described in the foregoing patents, pulse generator 100 generates pulses suitable for stimulation of neurons in body 10. The pulses generated by generator 100 are transmitted through conductors 102–105 to conventional conductor blocks 108 and 109 (FIG. 10). Surface 52, septum 70, wall 56, wall 58 and antenna 90 are arranged concentrically around an axis AX (FIG. 2).

Referring to FIGS. 1 and 3–8, a catheter 120 comprises an outer surface 122 defined by an outer tube 123. Catheter 120 has a semi-spherical distal end portion 124 and a proximal end portion 126. Catheter 120 includes a cylindrical central tube 128 that defines a fluid lumen 130 and a conductor lumen 132 that are coaxially arranged with respect to each other. Catheter 120 also includes isolation tubes 136–139 which electrically isolate lumen 132 from lumen 130. The isolation tubes are sealed to outer tube 123 or central tube 128 in the manner shown in FIGS. 3–7 by the following means:

Catheter 120 includes stimulation electrodes 150–153 that are exposed to body 10 at the outer surface of the catheter. Electrodes 150–153 are connected to catheter conductors 160–163, respectively. The conductors are contained within lumen 132, and therefore are electrically insulated from fluid lumen 130. Fluid lumen 130 transmits a fluid agent to body 10 through a conventional channel 170.

Figure 9:
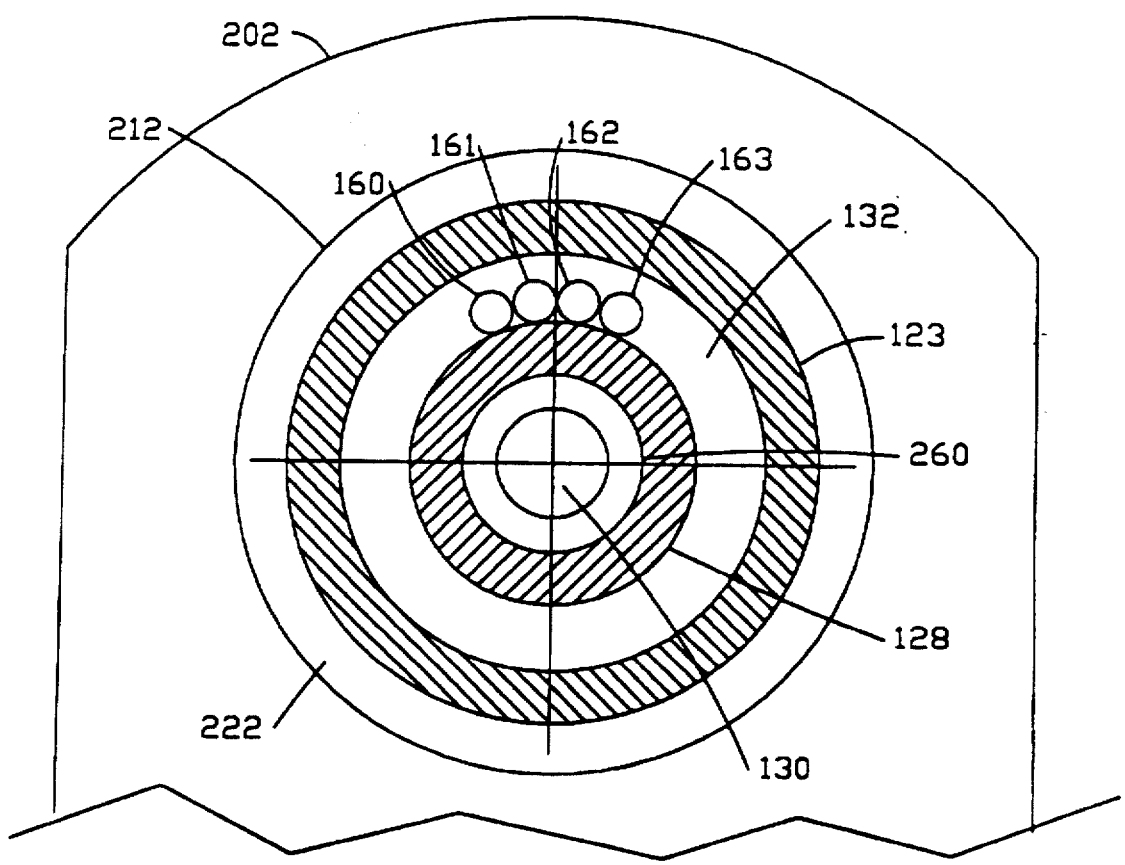
FIG. 9 is a cross-sectional view taken along line 9—9 of FIG. 10 with the cylindrical housing removed.

Referring to FIG. 1 and 10, the preferred embodiment also includes a connector assembly 180 comprising a cylindrical housing 182 having a distal end 184 and a proximal end 186. Housing 182 supports a connector block assembly 200 including blocks 202–205 defining openings 212–215, respectively. The openings are fitted with cylindrical sleeves 222–225 that are fabricated from metal and transmit signals from conductors 232–235 to terminals located in each of blocks 202–205, such as terminals 244–245 (FIGS. 5 and 6). Connectors 232–235 are connected to corresponding conductors 102–105, respectively. Conductors 232–235 are connected to metal sleeves 222–225 in the following manner:

Connector block assembly 200 also includes a fluid tube 260 (FIGS. 1 and 10) that is connected to outlet tube 82 and fluid lumen 130 of catheter 120. As shown in FIG. 9, tube 260 conducts fluid to lumen 130 while preventing the fluid from coming in contact with conductors 160–163. Assembly 200 includes a silicone covering to isolate the assembly from body tissue.

In operation, needle 14 is placed through antenna 20 and through skin 10 into membrane 72 of port 70. A fluid agent is supplied through needle 14 and port 70 into reservoir 80. A pump connected to coupling 16 provides sufficient pressure to cause the agent to flow through valve 83 in outlet tube 82 and into tube 260 of block assembly 200. The fluid agent then flows into lumen 130 of catheter 120 and ultimately through channel 170 to a predetermined portion of body 10.

The radio frequency power signals received by antenna 90 include flow control data signals that cause valve 83 to control the rate of flow of fluid agent 84 from reservoir 80 to catheter 120. Generator 100 includes a control section that generates control signals from the flow control data signals that are transmitted over conductor 86 to valve 83. Valve 83 enables the system to stop the flow of fluid agent from reservoir 80 when the stimulation is active. Or, if the specific therapy requires both therapies simultaneously, to allow the flow. The capability of coordination of function between the delivery of drug and electrical stimulation overcomes the disadvantage that each independently employed prior device would need to be controlled separately.

Housing 50 and catheter 120 are placed in body 10 by conventional surgical techniques so that the fluid agent is dispensed from channel 70 at the portion of the body requiring infusion of a fluid agent, such as a drug.

While the fluid agent is being administered to the body, neurostimulator 18 produces radio frequency energy signals that are communicated through antennas 20 and 90 to pulse generator 100. In a well-known manner, generator 100 produces electrical pulses suitable for stimulation of neurons in a body 10. Pulses are conducted through conductors 102–105, conductors 232–235 and metal sleeves 222–225 to four terminals in catheter 120 similar to terminals 244 and 245 shown in FIGS. 5 and 6. The terminals are laser-welded to the metal sleeves and provide a positive conducting path for the stimulation pulses. The pulses are then conducted through conductors 160–163 of catheter 120 to electrodes 150–153, respectively. The electrodes are placed during a surgical procedure to provide optimum stimulation of the desired neurons in body 10.

Experience has shown that connector assembly 180 provides an economical and reliable technique for transmitting both electrical stimulation pulses and a fluid agent to catheter 120. The construction of outer tube 123 and central tube 128, in combination with isolation tubes, such as 136–139, provides for a reliable electrical path from pulse generator 100 to electrodes 150–153. In addition, the arrangements shown in the drawings are easy to assemble and low in cost.

By using the foregoing techniques, both drug infusion and electrical stimulation therapy can be applied for periods of six to twelve months with a degree of reliability and cost effectiveness unattainable by known prior devices. These advantages are realized in part through the continuous flow of fluid agent through reservoir 100 without the use of any implanted pump and the ability of pulse generator 100 to produce stimulation pulses without the need for any implanted source of energy.

Housing 50 preferably is made from semi-rigid silicone, and port 70 preferably is fabricated from a steel mesh one-way fill port or in a bioacceptable epoxy. This feature eliminates the need for a hermetic titanium can that is currently required. Molded cylindrical housing 182 holds connection block assembly 200 and is sealed to housing 50 in a well-known manner. Thus, housing 50 and housing 182 are both sealed to prevent body fluid from entering their interiors.

Those skilled in the art will recognize that the preferred embodiments may be altered or amended without departing from the true spirit and scope of the invention as defined in the accompanying claims.

We claim:

1. An implantable system for infusing a fluid agent and providing electrical stimulation to a body using a source of fluid pressure and a source of electrical power both located external to said body, comprising:
   an implantable housing defining a first surface and a second surface;
   a percutaneous fill port located adjacent said first surface;
   an antenna located inside said housing for receiving radio frequency power signals;
   means located inside said housing and coupled to said antenna for generating stimulation pulses from said radio frequency power signals received by said antenna;
   a catheter defining an outer surface, a proximal end, a distal end and a fluid lumen for transporting said fluid agent through said catheter, said catheter comprising at least one electrode for administering electrical stimulation to a predetermined portion of said body, at least one catheter conductor for transmitting said stimulation pulses to said at least one electrode and means for transporting said fluid agent from said fluid lumen to a predetermined portion of said body;
   a reservoir located inside said housing and adapted to hold said fluid agent at a pressure maintained by a supply of said fluid agent admitted through said fill port for transmitting said fluid agent from said fluid lumen in the absence of a source of fluid pressure inside said housing; and
   connector means for transmitting said stimulation pulses from said means for generating to said at least one catheter conductor and for transporting said fluid agent from said reservoir to said fluid lumen, whereby said fluid agent and said electrical stimulation are administered to said body in the absence of a source of fluid pressure or electrical power inside said housing.

2. A system, as claimed in claim 1 wherein said first surface is smaller than said second surface and wherein said antenna is located adjacent said second surface.

3. A system, as claimed in claim 2, wherein said reservoir is located between said antenna and said first surface.

4. A system, as claimed in claim 3, wherein said means for generating is located between said antenna and said reservoir.

5. A system, as claimed in claim 1, wherein said radio frequency power signals comprise data signals.

6. A system, as claimed in claim 1, wherein said means for generating is powered by said radio frequency power signals.

7. A system, as claimed in claim 1, wherein said catheter further comprises a second lumen for carrying said at least one catheter conductor, said second lumen being electrically isolated from said fluid lumen.

8. A system, as claimed in claim 7, wherein said second lumen is coaxial with said fluid lumen.

9. A system, as claimed in claim 1, wherein said means for transporting comprises a channel between said fluid lumen and said outer surface of said catheter.

10. A system, as claimed in claim 1, wherein said connector means comprises a connector block assembly for each of said at least one catheter conductor, each said connector block assembly comprising:
    a block defining an opening;
    a metal sleeve located inside said opening; and
    a conductor coupled between said means for generating and said metal sleeve.

11. A system, as claimed in claim 10, wherein said catheter comprises a terminal coupled to each of said at least one cather conductor and extending through the outer surface of said catheter, each of said terminals being connected to said metal sleeve of one of said connector block assemblies.

12. A system, as claimed in claim 11, wherein said catheter further comprises a second lumen for carrying said at least one catheter conductor, said second lumen being electrically isolated from said fluid lumen and being located around said first lumen.

13. A system, as claimed in claim 12, wherein said connector means comprises a tube located inside said fluid lumen and extending through said opening of said connector block assembly for each of said at least one catheter conductor, said tube being coupled between said reservoir and said fluid lumen, whereby fluid is transported from said reservoir to said fluid lumen of said catheter while said stimulation pulses are being conducted to said at least one or more catheter conductor.

14. A system, as claimed in claim 1, and further comprising means for regulating the rate of flow of said fluid agent from said reservoir to said catheter.

15. A system, as claimed in claim 14, wherein said radio frequency power signals comprise flow regulating data signals for regulating the rate of flow of fluid agent from said reservoir to said catheter and wherein said means for generating said stimulation pulses further comprises means for controlling said means for regulating based on said flow regulating data signals.

16. A system, as claimed in claim 1, wherein said means located inside said housing and coupled to said antenna for generating stimulation pulses from said radio frequency power signals received by said antenna comprises a generator that is adapted to generate both stimulation pulses and control signals from said radio frequency power signals received by said antenna, and wherein said implantable system further comprises a valve responsive to said control signals and located intermediate said reservoir and said catheter for regulating a rate of flow of said fluid agent from said reservoir to said catheter.

17. An implantable system for infusing a fluid agent and providing electrical stimulation to a body, comprising:
    an implantable housing defining a first surface and a second surface;
    a percutaneous fill port located adjacent said first surface;
    a reservoir located inside said housing for holding said fluid agent at a pressure maintained by a supply of said fluid agent admitted through said fill port;
    an antenna located inside said housing for receiving radio frequency power signals;
    means located inside said housing and coupled to said antenna for generating stimulation pulses from said radio frequency power signals received by said antenna;

a catheter defining an outer surface, a proximal end, a distal end, a fluid lumen for transporting said fluid agent through said catheter, and a second lumen electrically isolated from said fluid lumen and being located around said first lumen, said catheter comprising at least one electrode for administering electrical stimulation to a predetermined portion of a body, at least one catheter conductor carried in said second lumen for transmitting said stimulation pulses to said at least one electrode, a terminal coupled to each of said at least one catheter conductor and extending through said outer surface of said catheter, and means for transporting said fluid agent from said fluid lumen to a predetermined portion of a body; and connector means for transmitting said stimulation pulses from said means for generating to said at least one catheter conductor and for transporting said fluid agent from said reservoir to said fluid lumen, said connector means comprising a connector block assembly for each of said at least one catheter conductor, each said connector block assembly comprising a block defining an opening, a metal sleeve located inside said opening and connected to said terminal of one of said at least one catheter conductor, and a conductor coupled between said means for generating and said metal sleeve, said connector means further comprising a tube located inside said fluid lumen and extending through said opening of said connector block assembly for each of said at least one catheter conductor, said tube being coupled between said reservoir and said fluid lumen, whereby fluid is transported from said reservoir to said fluid lumen of said catheter for administration to said body while said stimulation pulses are being conducted to said at least one catheter conductor, in the absence of a source of fluid pressure or electrical power inside said housing.

* * * * *

UNITED STATES PATENT AND TRADEMARK OFFICE
CERTIFICATE OF CORRECTION

PATENT NO.    : 5,697,951
DATED         : Dec. 16, 1997
INVENTOR(S) : Stanley D. Harpstead et al.

It is certified that error appears in the above-identified patent and that said Letters Patent is hereby corrected as shown below:

C. 6 L. 14    "one cather conductor" to be changed to "one catheter conductor"
C. 6 L. 31    "at least one or more catheter" to be changed to "at least one catheter"

Signed and Sealed this

Thirtieth Day of November, 1999

Attest:

Q. TODD DICKINSON

*Attesting Officer*     Acting Commissioner of Patents and Trademarks